United States Patent [19]

Chibnik et al.

[11] 3,945,933

[45] Mar. 23, 1976

[54] METAL COMPLEXES OF NITROGEN COMPOUNDS IN FLUIDS

[75] Inventors: Sheldon Chibnik, Cherry Hill; Ferdinand P. Otto, Woodbury, both of N.J.

[73] Assignee: Mobil Oil Corporation, New York, N.Y.

[22] Filed: July 31, 1974

[21] Appl. No.: 493,358

[52] U.S. Cl. .................. 252/33.3; 44/66; 44/68; 44/71; 252/35; 252/50; 252/75
[51] Int. Cl.$^2$. C10M 1/40; C10M 3/34; C10M 5/22; C10M 7/38
[58] Field of Search ............... 252/33.3, 75, 35, 50; 44/66, 68, 71

[56] References Cited
UNITED STATES PATENTS 3,755,167  8/1973  Otto et al............................ 252/33.3

*Primary Examiner*—Delbert E. Gantz
*Assistant Examiner*—I. Vaughn
*Attorney, Agent, or Firm*—C. A. Huggett; R. W. Barclay; S. A. Strober

[57] ABSTRACT

Multiple metal complexes of nitrogen compounds are prepared by reacting in any desired order (1) an organic reactant, preferably an alkenylsuccinic acid or anhydride or a polyalkylphenol-aldehyde reaction mixture, or a halogenated polyolefin; (2) a polyamine, having one nitrogen atom reactive with the organic reactant and at least one additional nitrogen atom such as an ethylene polyamine and the imidazoline or imidazolidine derivative thereof; (3) and at least two metal compounds, one of which is a metal of Groups IB, IIB, IVA, IVB, VIB, VIIB or VIII of the Periodic Table, capable of both forming a coordinated complex of the Werner type with the polyamine and also forming a complex with the second metal compound, and the said metal compound of metals of the above groups plus alkali and alkaline earth metals. The reactants may be reacted in any order, such as the above order, or the amine reactant may be precomplexed. Lubricant, grease, fuel and aqueous compositions are provided detergency and anti-wear properties by the presence of these multiple complexes.

15 Claims, No Drawings

METAL COMPLEXES OF NITROGEN COMPOUNDS IN FLUIDS

BACKGROUND OF THE INVENTION

1. Field of the Invention this invention relates to metal complexes of nitrogenous compounds and in particular to novel complexed reaction products, their method of preparation and their use in industrial fluids.

2. Description of the Prior Art

Single metal complexes of nitrogenous compounds have been described in U.S. Pat. Nos. 3,306,908, 3,624,115, 3,642,847, 3,649,659, 3,649,661 and 3,755,167. 3,163,603 refers to succinamic metal salts; and 3,346,493 describes single metal complexes. However, none of these references discloses forming a multiple (metal salt)-nitrogenous complex of the present invention.

SUMMARY OF THE INVENTION

It has now been discovered that a multiple metal salt complex of an organic substituted nitrogenous compound may be prepared by reacting an organic compound, an amine containing at least two nitrogen atoms and at least two metal compounds, at least one being a metal salt capable of forming a complex with the amine and also capable of forming a complex with the said second metal compound.

DESCRIPTION OF SPECIFIC EMBODIMENTS

More specifically, at least four different reactants make up the formation of the multiple metal complexes of this invention: a high molecular weight organic compound, an amine and two or more metal compounds.

1. ORGANIC REACTANT

It is known that the presence of hydrocarbyl groups are desirable for use in industrial organic fluids, such as lubricating oils. Perhaps because of the solubility in such fluids of long chain hydrocarbyl molecules, polar groups attached thereto may attract and hold suspensoids in the fluid readily during use, such as in an engine, an important function of dispersants. However, the shorter chain organic compounds provide some dispersancy and rust preventive properties, even in aqueous systems.

The preferred organic reactants of this invention include an alkenylsuccinic acid or anhydride, a reaction mixture of an alkyl phenol and aldehyde or a halogenated polyolefin; all are reactive with the amine reactant. In fact, any organic compound or mixture of such compounds capable of such reaction with an amine is suitable for the purpose of this invention. Monocarboxylic acids, dicarboxylic acids, and the like having at least 8 carbon atoms may be used.

Of the preferred species, the alkenylsuccinic anhydride is prepared by known reactions between an olefin and maleic anhydride. This reaction may be carried out thermally or by means of chlorination or by other means. Preferred olefins contain at least 8 carbon atoms, and preferably from about 14 to about 500 carbon atoms. Such olefins as polypropylene, polybutylene, polyisobutylene, or mixtures thereof are the most suitable. The resulting anhydride may be reacted with the amine to form the monoamide or the imide by the removal of one or two moles of water of condensation, respectively.

The second preferred organic reactant is an alkyl phenol which, in combination with an aldehyde, reacts with an amine to produce a Mannich base. The mechanism of this reaction is described in U.S. Pat. No. 3,368,972. Essentially, the phenol, amine and aldehyde are reacted together to form methylene bridges between amine and phenol, such as:

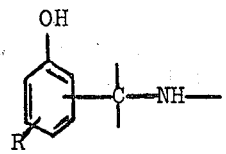

Substituted phenols include octylphenol, decylphenol, dodecylphenol, hexadecylphenol, eicosylphenol, and the like. Preferably the alkyl substituent R is a polymer of a $C_3$ to $C_5$ olefin, such as polypropylene, polybutylene, polyamylene; however, R may be a polymer of olefins of up to about $C_{16}$, including dimers, trimers and higher polymers of hexene, decene and dodecene. Also suitable are sulfur-bridged and oxygen-bridged phenols in which at least one aromatic ring contains the alkyl group, such as

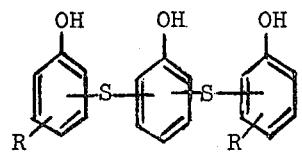

R being the alkyl group of 8 to about 500 carbon atoms. Other alkyl groups may be present on the phenol, regardless of chain length, but having preferably from 1 to 20 carbon atoms, providing that at least one extractable hydrogen atom be available for condensing with the aldehyde and amine. Naphthols are also suitable, both alpha and beta naphthols, the alkyl group R being attached to the ring by similar alkylating methods as with phenols. Hereinafter, unless specific compounds are referred to, the term "phenol" is understood to include naphthols and polyhydroxyaromatic compounds. Thus catechol, cresol, xylenol, hydroxydiphenyl, resorcinol and hydroquinone are considered "phenols" herein.

Alkylation methods are known (as in U.S. Pat. No. 3,368,982) and are not considered part of this invention. The useful aldehydes are the alkyl and aryl aldehydes of 1 to 30 carbon atoms, such as formaldehyde, acetaldehyde, propionaldehyde and benzaldehyde.

Halogenated polyolefins containing from 20 to 500 carbon atoms are also suitable reactants in this invention, particularly chlorinated polybutenes.

The most preferred reactants are those in which the alkenyl group of the succinic acid or anhydride and the alkyl group of the phenol are derived from polypropylene or polybutylene and have a molecular weight ranging from 200 to about 4000, more usually 500 to about 3000.

2. AMINE REACTANT

The amine reactant of this invention contains at least tow nitrogen atoms. Most preferred is an alkylene polyamine or a monocarboxylic acid or aldehyde derivative thereof. The alkylene polyamines have the generic formula $H_2N(R'NH)_n-H$ wherein $R'$ is an alkylene of 2 to 5 carbon atoms and n is an integer of 1 to about 10. Typical amines of this structure are ethylenediamine, diethylenetriamine, triethylenetetramine, tetraethylenepentamine, propylene diamine, di(methylethylene)triamine, hexapropyleneheptamine, and the like. Reaction mixtures obtained from commercial reactions in the preparation of ethylene polyamines are also acceptable if the required number of nitrogen atoms are available for reaction herein.

Also suitable are phenylenediamine, naphthalenediamine, benzidine, tolidine and other arylene polyamines and piperazine.

The acid or aldehyde derivatives of the alkylene polyamines are well known. U.S. Pat. No. 3,445,386 describes succinimide-amides, succinimide-imidazolines and succinimide-imidazolidines. U.S. Pat. No. 2,586,876 discloses the manner of preparing acid derivatives of polyamines. However, since the final products of this invention are understood to be double complexes, the initial alkylene polyamine should have sufficient —NH— groups available for complexing. The following structures are understood to occur in reaction with monocarboxylic acids, $R''COOH$:

a. aminoamide

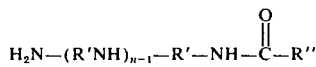

with the removal of one mole of water; and b. aminoimidazoline

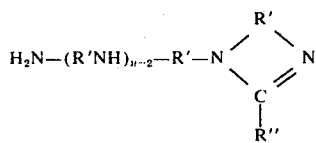

with the removal of two moles of water, wherein $R''$ is hydrogen or hydrocarbyl, i.e., alkyl, alkenyl, aryl, aralkyl or alkaryl of 1 to 30 carbon atoms. The integer $n$ must therefore be greater than 1 for the amide derivative, and greater than 2 for the imidazoline. Both amide and imidazoline may be present in the reaction mixture. In the reaction with the aldehyde $R''CHO$, the product is:

c. aminoimidazolidine

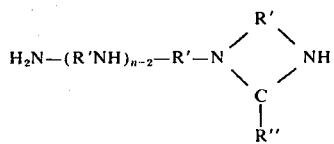

In this derivative, the imidazolidine ring contains an —NH— group available for forming a metal complex, hence n may be 2 or more. Whether the polyamine, amino-amide, amino-imidazoline or amino-imidazolidine is used, the most desirable starting material is tetraethylene pentamine for reasons of supply and cost.

Desirable acids include formic, acetic, butyric, valeric, stearic, oleic, benzoic and the like. The aldehydes include formaldehyde, paraformaldehyde, acetaldehyde, butyraldehyde, capraldehyde, benzaldehyde and the like.

3. COORDINATED COMPLEX METAL REACTANT

This reactant may be the salt of any metal of Groups IB, IIB, IVA, IVB, VIB, VIIB or VIII of the Periodic Table. The salts are derived from any organic or inorganic or hydrocarbyl-substituted inorganic acids. Both mono and polycarboxylic acids are suitable in this invention.

The preferred salts are those of the following acids:
a. $R'''(COOH)_n$
b. Sulfuric or sulfurous
c. Nitric
d. Organosulfonic acids, $R'''—SO_3H$;
e. Organophosphoric acids, $(R'''O)_2—P—OH$;
f. Organophosphinic or phosphonic acids;

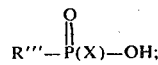

wherein $n$ is 1 or more; $R'''$ is hydrogen alkyl, alkenyl, aryl, aralkyl, alkaryl and amino and hydroxy forms thereof; and X is $R'''$, hydrogen or hydroxy having from 1 to about 300 carbon atoms.

Of greatest interest in this invention are salts of the organosulfonic acids, such as methane sulfonate, phenyl sulfonate, toluene sulfonate, and $C_{12}+$-alkyl-substituted phenylsulfonate, e.g. waxbenzene sulfonate, phenolsulfonate, and polyphenolsulfide sulfonate. Formic, acetic, propionic, butyric, valeric, caproic, caprylic, capric, benzoic and the like are also suitable. Dicarboxylic acids may be used, such as oxalic, malonic, succinic, glutaric, and the like. Also, alkylsuccinate, polyacrylic acid salts and styrene-maleic acid salts (wherein n can be up to 100) may be used.

The preferred metals are zirconium, cadmium, chromium, manganese, cobalt, nickel, copper, zinc, vanadium, tin, and iron; zinc being most preferred.

4. METAL REACTANT

The same metals set forth for reactant (3) may be used for metal reactant (4) and in addition alkali and alkaline earth metals. As used in this invention, for the sake of convenience, the term "metal reactant (4)" is intended to mean any of the metal salts of the acids used for reactant (3) and also metal oxide or hydroxide or halide. The acids most useful are monocarboxylic acids having from 1 to about 30 carbon atoms. Calcium, magnesium and zinc are the most preferred of the metals, and calcium acetate, magnesium acetate, magnesium hydroxide and zinc acetate are preferred complexing agents. Sodium, lithium and barium are other desirable metals; sodium hydroxide is of particular interest in this group.

One method of preparing the multiple complexes of this invention involves reacting the organic compound (1) with the amine reactant (2) first followed by reactions with metal reactants (3) and (4). Another route is to form an initial complex between the amine and metal reactant (3). In either case, reaction of the amine (or metal-amine complex) with alkenyl-succinic anhydride produces the succinamide upon removal of one mole of water of condensation per mole of anhydride; the removal of two moles leads to the succinimide. If an alkylene polyamine is used as the amine reactant, two moles of alkenylsuccinic anhydride per mole of amine could result in the formation of the bis(alkenylsuccinimide)

(a)
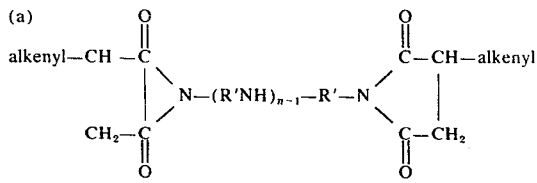

Similarly, reaction with two moles of both alkylphenol and aldehyde and one of amine could lead to preparation of the Mannich base.

(b)
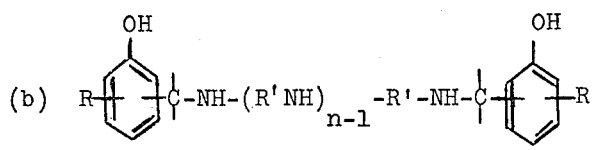

wherein the dangling valences are the remainder of the aldehyde reactant and R, R' and $n$ are as identified.

Mono-substituted forms of the above intermediate products are also useful herein:

(c)
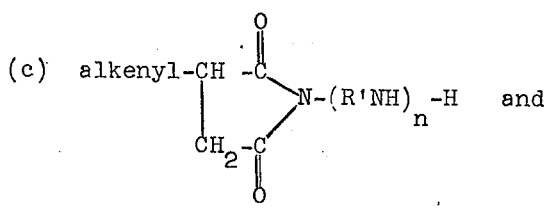 and (d)
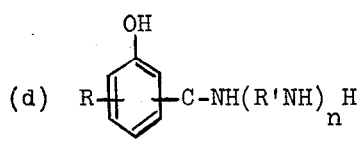

These mono-substituted products may also be formed with the amine derivatives, aminoamide, aminoimidazoline and aminoimidazolidine.

Reactions between the polyamine and either the monocarboxylic acid or its anhydride or the aldehyde to produce these derivatives may be carried at temperatures ranging from about 80° to about 250°C., and preferably 100° to 200°C. These temperature ranges are also used in the reaction between the amine reactant and the organic reactant.

For the sake of illustration, if the amine reactant and the organic reactant were initially reacted, the intermediate alkenylsuccinimide (either mono or bis) or alkenylsuccinimide-amide, alkenylsuccinimide-imidazoline or alkenylsuccinimide-imidazolidine or the corresponding Mannich base intermediate product is then reacted with metal reactant (3). The formation of the coordinated complex is carried out at a temperature of from 20° to about 250°C. using at least 0.25 mole, and preferably 0.5 to 3 moles, of metal salt per unreacted nitrogen atom of amine reactant, and preferably up to one mole. Clearly, not all of the available nitrogen atoms need be complexed; however, if the presence of maximum metal content is of importance in the particular utility of the final product, higher proportions of metal:nitrogen atom may be employed. Excess metal salt (3) may even remain with the complex in the fluid medium, such as a lubricating oil or grease.

As discussed previously, reactant (3) is the preferred first complexing salt. Of these, the organosulfonic acid salts are most preferred. Metal salts of alkylsulfonates, alkylphenylsulfonates and other aromatic sulfonates may be used. Organophosphates and organophosphonates also may be used. This complexing reaction is then followed by reaction with reactant (4).

Reactant (4) is the metal salt of a carboxylic acid or metal oxide or hydroxide, or metal inorganic salt. The metal of reactant (4) may be the same as or different from that of reactant (3). Acetates are the preferred salts for this reaction. It is theorized that the complexing occurs at the site of reactant (3) rather than on the nitrogen atoms, although this invention is not limited to any particular reaction mechanism. These double complexes permit the final products to contain increased metal values.

As indicated previously, our more preferred reaction route involves preparing an initial metal-amine complex by reacting amine reactant (2) with metal reactant (3), preferably the metal organosulfonate. This reaction product is then reacted with reactant (1), preferably the alkenylsuccinic acid or anhydride, with sufficient heating to produce the corresponding product, e.g. the single-complexed succinimide. Finally, reactant (4) is reacted with that product to yield the final double complex. Another preferred route is to react both reactants (3) and (4) with amine reactant (2), followed finally with formation of the succinimide or Mannich base.

A further modification is to react a metal oxide or metal hydroxide with the alkenylsuccinic anhydride of reactant (1), in sufficient amounts to form a monometal succinate, for instance zinc alkenylsuccinate. This metal salt typifies a metal dicarboxylate reactant useful as reactant (3). It is reacted with amine reactant (2) providing a zinc succinamide of the polyamine. Thereafter, another metal reactant (4) may be reacted to form the final complex. It is theorized that the zinc of the succinate forms a complex with a nitrogen atom of the same molecule or a different molecule.

The products of this invention have utility as dispersants, detergents and neutralizing compounds for industrial fluids, such as lubricants, both lube oils, including mineral oils, synthetic oils, such as synthetic ester oils, polyphenyl ethers, polyglycol ethers, synthetic hydrocarbons and the like, and greases made therefrom, cutting fluids and hydraulic fluids, both oil and water-containing systems, such as fire-resistant hydraulic fluids, and in fuels, such as gasolines and fuel oils; also transmission fluids and heat exchange liquids may also require the presence of such additives. These complexes also provide anti-wear properties to lubricants.

This invention is better illustrated by the following working examples, in which the parts of materials are on a weight basis.

EXAMPLE 1

Alkyl ($C_{15}$—$C_{20}$) benzene sulfonic acid (5120 parts) was placed in a reaction vessel and was degassed at room temperature by purging with nitrogen for 2 hours. Then 600 parts of water and 300 parts of zinc oxide were added over 1 hour at about 50°C. The reaction temperature was raised to 100°C. in about 1 hour while bubbling nitrogen in, during which time water was entrained and removed, and 1540 parts of a process oil was added. Stripping of water was continued until a temperature of 150°C. was reached (2 ½ hours). Final stripping of water was accomplished at 150°C. under a vacuum of 9 mm. of Hg. The product, filtered through Hyflo clay, had the following analysis:

|  | % Calculated | % Found |
|---|---|---|
| Zinc | 3.60 | 3.58 |
| Sulfur | 3.50 | 3.22 |

The alkylbenzene is a mixture of 60% monoalkylbenzene and 40% dialkylbenzene derived from a mixture of $C_{15}$–$C_{20}$ olefins. The process oil used in this and subsequent examples is a refinery process oil produced by the furfural extraction of a high paraffin feed stream. It has low aromatic and naphthenic contents and a very low percentage of sulfur. Its viscosity is such that the oil is suitable as a solvent in certain commercial operations.

EXAMPLE 2

The zinc alkylbenzene sulfonate of Example 1 (20.6 parts), 2.4 parts of an alkylene polyamine having an average composition of tetraethylenepentamine and 10.0 parts of process oil were placed in a suitable reaction vessel and reacted at 150°C. for 2 hours. To the resulting product was added 47.52 parts of polybutenylsuccinic anhydride (made from maleic anhydride and polybutene having a molecular weight of 1350) in about 30 minutes, followed by slowly applying vacuum to the vessel. The reaction was continued for 2 ½ hours at 150°C. at a vacuum of 15–25 mm. of Hg. The product was a clear, dark brown, viscous oil having 0.99% N (calculated 1.0%), 0.94% Zn (calculated 0.91%) and 1.03% S (calculated 0.90%). It has a Total Base Number of 18.0 mg. KOH/gm., a Total Acid Number of 20.7 mg. KOH/gm. and a KV at 210°F. of 551.

EXAMPLE 3

To 133 parts of the product of Example 2 was added 117 parts of process oil and the mixture was combined, with stirring, with a solution of 4.4 parts of zinc acetate dihydrate in 20 parts of water at 90°C. for 1 hour. The water was removed by stripping at 150°C. for one hour and the resulting product was filtered. The filtered product analysis was: 1.07% zinc found (calculated, 1.03%). This experiment shows that the sulfonate-acetate combination can be used successfully to form the double complex.

EXAMPLE 4

In a suitable reactor, 150 parts of the product of Example 2 was mixed with a solution of 5.7 parts of zinc acetate dihydrate in 24 parts of water. The mixture was heated at 90°C. for one hour and then subject to stripping at 150°C. for one hour to remove water. The product was filtered. The zinc content was 1.56% found (calculated, 1.72%).

EXAMPLE 5

Using the same procedure as in Example 4, 11.4 parts of zinc acetate dihydrate in 48 parts of water was used. The product analysis, after filtration, was: 1.62% zinc found (calculated, 2.74%).

EXAMPLE 6

Using the same procedure as in Example 4, 1.33 parts of calcium acetate monohydrate was mixed with 100 parts of the product of Example 2 and 5 parts of water. The final product analysis was: 0.29% calcium found (calculated, 0.30%). When the same amount of calcium acetate was added to an oil solution containing a polybutenylsuccinimide of the polyamine without the sulfonate of Example 2 present, the amount of calcium acetate incorporated in the product was negligible.

EXAMPLE 7

Employing the same procedure and conditions as in Example 4, 3.2 parts of zinc oleate was mixed with 78.9 parts of the product of Example 2. After final filtration, the product had the following analysis:

|  | % Calculated | % Found |
|---|---|---|
| Zinc | 1.5 | 1.03 |
| Sulfur | 0.60 | 0.64 |
| Nitrogen | 0.54 | 0.48 |

EXAMPLE 8

In a suitable reactor, 264 parts of the zinc alkylbenzene sulfonate of Example 1, 32 parts of zinc acetate dihydrate and 128 parts of water were mixed together in 468 parts of process oil at 90°C. for 1 hour. To the resulting mixture was added 31 parts of an alkylene polyamine having an average composition of tetraethylene pentamine and this mixture was heated at 90°C. for 1 hour. The polybutenylsuccinic anhydride of Example 2 (714 parts) was mixed into the reaction mass and the mass was heated to 150°C. and held until the water added and formed by condensation was removed. The resulting mixture was held at 150°C. for 2 hours at 3 mm. Hg. vacuum, then filtered. The product was a clear, dark viscous oil having the following analysis:

|  | % Calculated | % Found |
|---|---|---|
| Zinc | 1.26 | 1.22 |
| Sulfur | 0.59 | 0.76 |
| Nitrogen | 0.69 | 0.68 |

This example shows that the two metal salts may be prereacted prior to reaction with amine.

EXAMPLE 9

A commercial zinc salt prepared from an alkenylsuccinic anhydride and an alkylene polyamine having an average composition of tetraethylene pentamine is used in this example. The salt may be prepared by a procedure generally described in U.S. Pat. No. 3,163,603. The salt contains 1.6% zinc and 0.7% nitrogen.

To 1500 parts of the zinc salt and about 2380 parts of a process mineral oil was added 80.6 parts of zinc acetate dihydrate in 160 parts of water at 90°C. and the mixture held at that temperature for 1 hour. The water in the reaction mixture was removed by stripping at 150°C. for 1 hour, and the resulting product was filtered. The product analysis was: 2.98% zinc found (calculated, 3.10%).

EXAMPLE 10

Following the same procedures as in Example 9, 6 parts of mineral oil was mixed with the commercial zinc salt and process mineral oil. To this mixture was added 38.3 parts of a solution of zinc methane sulfonate solution prepared by mixing 3 parts of zinc oxide, 10.3 parts of an aqueous solution of 70% by weight of methane sulfonic acid and 25 parts of water at 25°C. The reaction mixture was heated at 150°C. for 1 hour and then filtered. The product had the following analysis: 3.07% zinc found (calculated, 2.9%) and 1.52% sulfur found (calculated, 1.4%).

EXAMPLE 11 a. Two thousand parts of polypropylphenol (made from phenol and polypropylene of 825 molecular weight), 92.5 parts of diethylenetriamine and 717 parts of process mineral oil were charged to a flask, and 90 parts of paraformaldehyde was added to the mixture over 1 ½ hours at 80°C. This mixture was refluxed for 1 ½ hours at about 100°–105°C. The water was removed by purging with nitrogen for 30 minutes up to 150°C, and then a vacuum of 5 mm of Hg was applied for 2 hours at 150°C. The product had the following analysis:

|  | % Calculated | % Found |
| --- | --- | --- |
| Nitrogen | 1.30 | 1.27 |

Two thousand parts of the resulting product, 650 parts of the zinc alkylbenzene sulfonate of EXample 1 and 100 parts of distilled water were mixed and heated for 2 ½ hours at 100°–146°C., during which time water was removed. This was followed by heating at 150°C. for 2 hours under 4 mm of Hg. The resulting intermediate complex product, containing about 31.2% oil, had the following analysis:

|  | % Calculated | % Found |
| --- | --- | --- |
| Nitrogen | 1.00 | 0.96 |
| Zinc | 0.86 | 0.85 |

Using the procedure of Example 4, 2650 parts of the above product, 78.5 parts of zinc acetate dihydrate and 150 parts of water were reacted as in Example 4 to form the double complex.

b. The zinc acetate and water are added to the reaction mixture with the zinc alkylbenzene sulfonate, instead of producing the intermediate single complex product. The double complex is thereby prepared in a single step.

EXAMPLE 12

A commercial polybutylpolyamine, containing 4.15 percent by weight of nitrogen and a molecular weight of about 1539, prepared from a halobutylene polymer and an alkylene polyamine having an average composition of tetraethylene pentamine, according to procedures generally disclosed in U.S. Pat. No. 3,438,757, is used in this example.

In a suitable reactor, 170 parts of the polybutylpolyamine is dissolved in 73 parts of process oil and treated with 183 parts of the zinc alkylbenzene sulfonate of Example 1, 22 parts of zinc acetate dihydrate and 100 parts of water at 90°C for 1 hour. The mixture is heated to 150°C to strip off its water and held at this temperature for 2 hours under 4 mm Hg vacuum. The product is filtered.

EXAMPLE 13

In a suitable reactor are added 714 parts of the alkenylsuccinic anhydride of Example 2, 264 parts of zinc alkylbenzene sulfonate of Example 1, 28 parts of an alkylene polyamine having an average composition of tetraethylene pentamine, 32 parts of zinc acetate in 128 parts of water, and 1030 parts of process oil. The reaction mixture is held at 90°C. during the addition. Then, the mixture is heated to 150°C. and held for 1 hour. Water of addition and condensation is removed by stripping to 150°C. at 3 mm. Hg. vacuum. The final product is filtered.

EXAMPLE 14 a. Into a suitable reaction vessel was placed 4.71 parts of an alkylene polyamine having an average composition of tetraethylene pentamine and 15 parts of a solvent-refined paraffinic oil having an SUV of 100 seconds at 100°F. To this was added 1.52 parts of acetic anhydride with agitation. The mixture was held under a vacuum of about 35 mm Hg and heated at 150°C for 30 minutes.

b. Alkyl ($C_{13}$—$C_{20}$) benzene sulfonic acid (5,120 parts), having 1.29 meq./g. total acidity, was degassed at room temperature for 2 hours by purging with nitrogen. 600 cc. of water was added to the mixture, followed by the addition in 1 hour at about 50°C of 300 parts of zinc oxide. The reaction temperature was raised to 100°C in about 1 hour while bubbling in nitrogen. Some water was removed in this step. 1,540 parts of Promor No. 5 process oil was added and stripping of water was continued until a temperature of 150°C was reached (about 2 ½ hours). Heating and stripping was continued for 3 additional hours at 150°C under a vacuum of 9 mm Hg. The product, zinc alkyl ($C_{13}$—$C_{20}$) benzene sulfonate, filtered through Hyflo clay, had the following analysis:

|  | % Calculated | % Found |
| --- | --- | --- |
| Zinc | 3.60 | 3.58 |
| Sulfur | 3.50 | 3.22 | c. One hundred and seven (107) parts of (a) product 700 parts of (b) and 427 parts of process mineral oil were placed in a suitable reactor, heated to 150°C and held there for 2 hours; then 1,875 parts of polypropenylsuccinic anhydride (prepared from maleic anhydride and polypropene having a molecular weight of 1,120) was added and this reaction mixture was heated for 3 hours under a vacuum of 5 mm of Hg and 150°C. A clear, dark brown product was produced having the following analysis:

|  | % Calculated | % Found |
| --- | --- | --- |
| Nitrogen | 0.91 | 0.95 |
| Zinc | 0.77 | 0.78 |
| Sulfur | 0.77 | 0.75 |

The alkylbenzene referred to in part (b) above is a mixture of 60 percent monoalkyl benzene and 40 percent dialkyl benzene derived from a mixture of $C_{13}$—$C_{20}$ olefins.

d. A solution of 85 parts of zinc acetate dihydrate in 200 parts of water is mixed with 3109 parts of the product of part (c) and stirred at 95°C for 1 hour. The water is removed by stripping to 150°C under vacuum.

EVALUATION OF PRODUCTS

A number of the products of this invention was subjected to evaluation as lubricant additives.

Two of the evaluation tests are (1) Sulfuric Acid and (2) Pyruvic Acid Tests. The procedures are as follows:

1. The Sulfuric Acid Neutralization Test

This test measures the ability of an oil additive to neutralize strong acids formed in the engine operating on sulfur containing fuels. Sulfuric acid is mixed with a heated blend of the additive and the oil in iso-octane. The solution is centrifuged to separate out insoluble material. The optical density of the clear solution is measured. From this value, the optical density of a blend of the additive applied to a corresponding amount with iso-octane is subtracted; the difference gives the optical density of dispersed sulfuric reaction products. The optical density of an acetone extraction of the iso-octane-oil solution is then determined. The average optical density of the iso-octane-oil solution is expressed as the optical density of the dispersed sulfuric acid reaction products. The average optical density of the acetone solution is expressed as the optical density of the non-dispersed sulfuric reaction products. The total of these values or either one alone is used in the evaluation of detergent additives. The lower the value of this test, the better the detergent.

2. Pyruvic Acid Dispersion Test

This test measures the dispersant value of an oil additive and indicates the detergent properties when used in lubricating engines operating on low sulfur compound fuels. The values of this test are taken with those of the sulfuric acid test to predict the performance of these additives. Pyruvic acid is mixed with a heated blend of the additive and oil. The mixture is diluted with benzene and centrifuged to separate the insoluble materials. The insolubles are dissolved in acetone. The optical density of the oil-benzene solution gives the total amount of color. From this value, the optical density of the initial additive blend diluted with benzene to a corresponding amount is subtracted. This corrected value is expressed as the optical density of the dispersed pyruvic acid polymer. The optical density of the acetone solution is expressed as the optical density of the non-dispersed pyruvic acid polymer. The higher the percentage of the pyruvic acid results, the better the additive.

The test samples for both procedures consist of a solvent-refined mineral oil of SAE 30 grade containing 3% by weight of active ingredient of the additive and 1% by weight of zinc dihexylphosphorodithioate. The results are as follows:

| Product (Example) | Pyruvic Acid Test | Sulfuric Acid Test |
|---|---|---|
| None | 58.6 | 0.102 |
| 3 | 99.2 | 0.04 |
| 5 | 99.3 | 0.005 |
| 8 | 99.7 | 0.010 |

3. In another evaluation of detergency, a lubricating oil containing the complex salt and other additives are tested in a Caterpillar engine. The lubricant composition consists of solvent-refined paraffinic neutral and bright oils blended to provide a 62 to 64 SUS with 2.7% by weight of the complex, 1% of a barium salt of phosphosulfurized polybutene, 1.2% zinc-isopropyl-ethylhexylphosphorodithioate and 1.3% of overbased magnesium alkylbenzene sulfonate having a total base number of 400.

The engine is a single-cylinder, 4-cycle engine operating under the following conditions:

| | |
|---|---|
| Speed, rpm | = 1800 |
| Oil Temp., °F. | = 205 |
| Jacket Temp. °F. | = 190 |
| Fuel | = Diesel fuel containing 0.4% sulfur |
| Operating Time, hrs. | = 120 |

At the completion of the test, the piston is removed and examined for carbon and lacquer deposits. The following results were obtained:

| Example of Complex Tested | Piston Rating (100=clean) | Lacquer Demerits | % Top Groove Packing |
|---|---|---|---|
| None | 43.5 | 39.0 | 84 |
| 2 | 82.3 | 10.5 | 62 |
| 3 | 82.8 | 10.5 | 55 |
| 4 | 84.4 | 10.2 | 29 |
| 6 | 84.3 | 8.7 | 67 |

The single complex of Example 2 provides very good detergency properties, products of Examples 4 and 6 had higher piston ratings and the Example 4 product gave a top groove packing of 29%.

4. In a further test, an aluminum cylinder is heated by radiant energy in an enclosed vessel. The surface temperature of the cylinder is maintained at 575°F. during the 70 minutes of the test. The cylinder rotates at 2 rpm. in an oil bath and the thin oil film forming on the cylinder comes into contact with a heated atmosphere (350°F.) containing air causing oxidation of the film and oxidation deposits. The rating is based on the amount of deposits forming on the cylinder surface (100 is totally clean). The oil formulation is the same as that of Test (3).

The ratings are as follows:

| Example of Complex Tested | Rating |
|---|---|
| 2 | 76 |
| 4 | 82 |
| 6 | 93 |

Again the result for the single complex product of Example 2 is fairly acceptable, but the products of Examples 4 and 6 provide even higher ratings.

EXAMPLE 15 a. In a suitable reactor were mixed 60 parts of polybutenylsuccinimide prepared from polybutenylsuccinic anhydride of 900 molecular weight and an amine having an average composition of tetraethylene pentamine was dissolved in 3.75 parts of a process oil. To the solution was added a solution of 3.6 parts of magnesium acetate tetrahydrate in 8 parts of water at 90°C. for 1 hour. The water was removed by heating at 150°C. for 1 hour at 3 mm. Hg. vacuum and the product was filtered. The product contained 0.03% magnesium, indicating that magnesium acetate alone does not complex.

b. In a suitable reactor 55 parts of a coordinated complex formed from nickel methanesulfonate, tetraethylene pentamine and polybutenylsuccinic anhydride (derived from polybutene having a 1350 molecular weight) similar to that as prepared in Example 2, was mixed with 45 parts of process oil diluent and 6.7 parts of a 25% solution of magnesium acetate in water. The reaction mixture was treated as in (a) above. The resulting product after filtration contained 0.35% nickel and 0.1% magnesium, three times the amount of the (a) product.

c. In a suitable reactor 75 parts of the nickel alkylbenzene sulfonate complex of the polybutenylsuccinimide of Example 2, 61 parts of oil diluent and 8.6 parts of a 30% magnesium acetate solution in water were mixed and reacted as (b) above. The resulting product contained 0.79% nickel and 0.26% magnesium.

The pyruvic acid and sulfuric acid test results of products (b) and (c) are as follows:

| Product | Pyruvic Acid Test | Sulfuric Acid Test |
|---|---|---|
| (b) | 98.1 | 0.002 |
| (c) | 99.7 | 0.002 |

EXAMPLE 16

In a suitable vessel were mixed 94 parts of phosphorus pentoxide and a mixture of mono and diesters of phosphoric acid prepared from 2600 parts of polypropylphenol (prepared by alkylating phenol with a polypropylene having a molecular weight of about 825). A solution of zinc salts was prepared by mixing 2450 parts of the above mixture, 108 parts of zinc carbonate and 850 parts of process oil. The said solution (1500 parts) was then mixed with 54 parts an amine having the average composition of tetraethylene pentamine, 713 parts of polypropenylsuccinic anhydride (produced from maleic anhydride and polypropylene having a molecular weight of 1120) and 256 parts of process oil. The mixture was heated to produce the coordinate complex as in the previous examples.

To 100 parts of the above coordinate complex was added 44 parts of zinc acetate dihydrate and 10 parts of water and the mixture was reacted as in the previous examples to produce the double complex. The product contained 1.82% zinc which corresponds to 1.89 moles of zinc acetate per mole of zinc polypropylphenol phosphate complex.

EXAMPLE 17

In a suitable reactor were mixed 3.7 parts of zinc methane sulfonate, 8.4 parts of water, 2.7 parts of tetraethylenepentamine, 56.6 parts of polybutenylsuccinic anhydride similar to that used in Example 2 and 51.1 parts of oil diluent. The mixture was reacted as in the previous examples and the product after filtering out insolubles contained 0.43% zinc and 0.47% sulfur.

To 100 parts of the above product were added 4.3 parts of zinc acetate dihydrate in 10 parts of water. The mixture was treated as in the previous example and after filtering the product contained 1.58% zinc equivalent to 2.8 moles of zinc salt added per mole of zinc complex in the starting material. The result of the oxidation deposit test (Evaluation Test 4), for this product was 97.

This invention has been described in narrow and broad terms and is understood to be susceptible of many minor modifications which may occur to those skilled in the art. Such modifications are deemed to be within the scope of our invention.

Having described our invention, we claim:

1. A fluid composition comprising a base fluid and a minor amount sufficient to provide detergent properties thereto of the reaction product formed at temperatures of from about 20°C. to about 250°C. of (1) an alkenylsuccinic anhydride, (2) an aliphatic polyamine, (3) a metal organosulfonate and (4) a metal carboxylate containing from 1 to 30 carbon atoms.

2. The composition of claim 1 wherein reactant (2) has the formula $$H_2N-(R'NH)_n-H$$

wherein $n$ is a number from 1 to 10 and $R'$ is alkylene of 2 to 5 carbon atoms.

3. The composition of claim 1 wherein reactant (1) has from 8 to 500 carbon atoms.

4. The composition of claim 2 wherein reactant (2) is an ethylene polyamine having an average number of nitrogen atoms equivalent to tetraethylene pentamine.

5. The composition of claim 1 wherein reactant (3) is a salt of a metal of Periodic Groups IB, IIB, IVA, IVB, VB, VIB, VIIB or VIII.

6. The composition of claim 5 wherein reactant (3) is a zinc salt.

7. The composition of claim 6 wherein reactant (3) is a zinc alkylbenzene sulfonate having at least 12 carbon atoms in the alkyl group.

8. The composition of claim 1 wherein reactant (4) is selected from the group consisting of zinc, alkali metal and alkaline earth metal carboxylates.

9. The composition of claim 1 wherein reactant (4) is zinc acetate.

10. The composition of claim 1 wherein reactant (4) is provided by reacting the alkenylsuccinic anhydride of reactant (1) with a metal oxide of hydroxide.

11. The composition of claim 1 wherein reactant (1) is an alkenylsuccinic anhydride having from 20 to 300 carbon atoms in the alkenyl group, reactant (2) is an ethylene polyamine, reactant (3) is zinc waxbenzene sulfonate and reactant (4) is zinc acetate.

12. The composition of claim 11 wherein reactant (2) and reactant (3) are reacted together to form a zinc waxbenzene sulfonate complex of the said polyamine and the complexed intermediate is reacted with reactant (1) to form the corresponding complexed alkenylsuccinimide and the resulting product is reacted with reactant (4) to form a double zinc acetate-zinc waxbene sulfonate complex of the succinimide of tetraethylene pentamine.

13. The composition of claim 11 wherein reactant (3) and reactant (4) are reacted to form a zinc acetate-zinc waxbenzene sulfonate complex, the said complex is then reacted with reactant (2) to form a complex of an ethylene polyamine and the resulting product is reacted with reactant (1).

14. The composition of claim 1 wherein the base fluid is selected from the group consisting of lubricating mineral and synthetic oils, gasoline, greases, hydraulic fluids and cutting fluids.

15. The composition of claim 14 wherein the base fluid is mineral lubricating oil.

\* \* \* \* \*